United States Patent [19]

Futami et al.

[11] Patent Number: 5,051,130

[45] Date of Patent: Sep. 24, 1991

[54] FILLING COMPOSITIONS FOR DENTAL TEMPORARY SEALING

[75] Inventors: Shunichi Futami, Nagareyama; Sueo Saito; Nobuko Okita, both of Tokyo, all of Japan

[73] Assignee: G-C Dental Industrial Corp., Tokyo, Japan

[21] Appl. No.: 413,071

[22] Filed: Sep. 27, 1989

[30] Foreign Application Priority Data

Oct. 11, 1988 [JP] Japan .................................. 253888

[51] Int. Cl.$^5$ .......................... A61K 6/06; C04B 28/28
[52] U.S. Cl. ................................... 106/35; 433/228.1; 523/116; 523/118
[58] Field of Search .................. 106/35; 523/116, 118; 433/228.1

[56] References Cited

U.S. PATENT DOCUMENTS

| | | | |
|---|---|---|---|
| 4,775,592 | 10/1988 | Akahawe et al. | 106/35 |
| 4,808,228 | 2/1989 | Randklev | 106/35 |
| 4,931,096 | 6/1990 | Fujisawa | 106/35 |
| 4,952,613 | 8/1990 | Hosoda | 106/35 |

Primary Examiner—A. Lionel Clingman
Attorney, Agent, or Firm—Oblon, Spivak, McClelland, Maier & Neustadt

[57] ABSTRACT

A filling composition for dental temporary sealing comprises a component A defined by a puttied base agent composition wherein a base agent containing a water-insoluble liquid acidic phosphate and/or a water-insoluble organic carboxylic acid that is liquid at room temperature contains 5.0 to 50.0 % by weight of finely divided silica, and a component B defined by a puttied setting agent composition wherein a setting agent containing a reactive multi-valent metal salt containing 1.0 to 20.0 % by weight of a finely divided inorganic filler having a solubility of 0.2 or less at 20° C.

3 Claims, No Drawings

FILLING COMPOSITIONS FOR DENTAL TEMPORARY SEALING

BACKGROUND OF THE INVENTION

1. Field of the Invention

The present invention relates to a filling composition for dental temporary sealing in dental treatments, which is used as a temporary sealant for the teeth required for the setting, sedation and resolution of oral inflammation.

2. Prior Art

Temporary sealants are inevitable for daily dental treatments, and are used for temporary sealing for the sedation of cavities after the removal of carious teeth and sealing of medicaments in endodontics.

Heretofore, temporary sealants have generally been broken down into the following three classes.

(1) Temporary stopping composed mainly of gutta-percha.
(2) Hydraulic temporary sealant.
(3) Zinc oxide-eugenol cement.

The temporary stopping has thermoplasticity and is supplied in the form of sticks or pellets.

For use, it is softened by heating and pressed against a cavity in a tooth for temporary sealing. Because of its easy-to-handle-property, the temporary stopping has been used for long. However, the temporary stopping is not so effective for border sealing of cavities due to its increased contraction upon hardening by cooling, its insufficient adhesion to the teeth and so on.

The hydraulic temporary sealants takes some time (several hours) to set, and shows poor adhesion to the teeth. For these and other reasons, it is not so effective for border sealing of cavities, and is removed from the cavities with considerable difficulty.

The requirements for temporary sealants are that:
(1) They are effective for border sealing of cavities.
(2) They are easily removed from cavities.
(3) Their setting time is short.

The zinc oxide eugenol cement is a material frequently used as the temporary sealant, since it possesses properties substantially accommodative to such requirements as mentioned above, excels in fluidity and has suitable strength and bonding force.

The zinc oxide eugenol cement is supplied in the form of:

(1) A combination of a powdery setting agent containing zinc oxide with a liquid base agent containing eugenol.
(2) A tube in which a combination of a zinc oxide-containing curing agent and an eugenol-containing base agent are filled in the form of a paste of high fluidity.

Problems with this material are that eugenol emits an odor peculiar to it, and that eugenol per se irritates mucosal tissues such that the pain becomes intolerable especially, in the case where there is inflammation or a hurt in the oral cavity.

In contrast, a non-eugenol base paste is a dental formable composition that is of no irritativeness at all, has no harmful influence upon pulpal tissues and set at room temperature for a short period of time, and is mainly used for temporary filling of deficiencies in the teeth. The non-eugenol having such properties provides a filling composition for dental temporary sealing which is preferable as a sealant.

Non-eugenol base materials have been available in paste/paste form and used particularly for root canal filling and as temporary bonding and impression materials.

The non-eugenol has thus been used also as a temporary sealant. Since the non-eugenol is in paste form, however, the mixing and kneading of a setting agent with a base agent have a serious influence upon the properties of the set product, because the mixing and kneading time differs depending upon the skillfulness of dental technicians and so does the dispersion state of both components. If the base agent and the zinc oxide-containing setting agent are in the form of a paste of high fluidity, it is then relatively easy to uniformly force the paste out of a tube on mixing pad for mixing. However, if the paste is used for temporary sealing of the teeth, considerable difficulty is then encountered in such temporary sealing because of difficulty experienced in its placing and forming due to its softness. Thus, the paste is usually difficult to handle.

Due to a comparatively soft nature of the set product, abrasion by occlusive action and by brushing are increased when temporarily sealed causing to deformation and dropping-off.

As stated above, when the setting and base agents are used in such powder/liquid or paste/paste form as conventionally carried out, their mixing are difficult. Further, the use of the putty-form zinc oxide eugenol cement using eugenol poses a problem difficult to solve because of its strong stimulativeness and harmfulness. However, it has now been found that when setting and base agents based on non-eugenol base materials are applied in putty form, they can be securely used with no harmful influence on the teeth at all, easily taken out in the desired amount by means of an exclusive spatula, and much easily mixed together and mixed up irrespective of skillfulness.

The putty-form setting and base agents according to the present invention shows a deformation of 10% (a diameter of 11 mm) or less with respect to the original diameter when a sample is forced out on a flat plate and, after 30 seconds, when measured its diameter with the use of an instrument (of 10 mm in diameter and 0.5 ml in volume) used for the measurement of the consistency of dental zinc phosphate cement according to JIS T 6602, and so has no substantial natural fluidity.

By making the setting and base agents in a form of a putty, it is very unlikely that the material may leach out of a package. Nor does any leakage of the material take place during use or storage. The material has also no harmful influence upon intra-oral tissues at all. Thus, the present invention assures sound clinic activities and are well expected to give no pain to patients.

For the purpose of making it in a form of a putty, finely divided silica and an inorganic filler having a solubility of 0.2 or less at 20° C. are added to the base and setting agents, respectively, thereby improving the wear resistance of the set product.

The non-eugenol base material is subjected to a promoted setting reaction by water and an acid and set by the setting reaction of a reactive multi-valent metal salt with an acidic phosphate or the saponification of a reactive multi-valent metal salt with a higher fatty acid.

The acidic phosphates used in the present invention are essentially insoluble in water and liquid at room temperature, and may include monoalkyl or monoaryl acid phosphates, dialkyl (or aryl) acid phosphates and alkyl aryl acid phosphates in which one or two of three hydrogen atoms of orthophosphoric acid is or are replaced by an alkyl or aryl group or groups. It is generally understood that the more the carbon atoms of the substituent, the lower the reaction rate becomes, but the less the carbon atoms, the higher the water solubility and the more sharp the reaction rate becomes.

Consequently, the size of the substituent applicable in the present invention is limited to a range of 3 to 13, as expressed in terms of the number of carbon atoms.

The reactive multi-valent metal salts usable in the present invention are di- or more-valent metal salts, viz., oxides, hydroxides, basic salts, silicates and the like of alkaline-earth metals such as magnesium, calcium, barium and strontium as well as aluminium and heavy metals such as zinc, bismuth, lead, nickel, iron and copper. Used advantageously to this end are salts essentially insoluble in water and capable of reacting with acids.

If required, small amounts of fluorine compounds, especially, slightly soluble fluorides, silicofluorides, titanium fluorides, zircon fluorides and so on may be added as the components capable of increasing the rate of setting reactions of the liquid acidic phosphates with the reactive multi-valent metal salts.

By using a liquid organic carboxylic acid having at least six carbon atoms as the organic carboxylic acid that is insoluble in water and liquid at room temperature, it is possible to improve the strength and toughness of the set products and afford the water resistance of fatty acid soap to them.

Suitable as setting aid components are mono-, di- or more-valent organic carboxylic acid having five or less carbon atoms, and suitable as reinforcing components for affording viscosity for the smooth progress of setting reactions are carboxyl group-containing rosins, rosin derivatives, maleic resins, acidic maleic resins and so on. If required, such thermoplastic resins as petroleum resins, ethyl cellulose, vinyl acetate, ethylene/vinyl acetate copolymers, ester rubber and so on may be further added.

According to the present invention, finely-divided silica and a finely-divided inorganic filler having a solubility of 0.2 or less at 20° C. are added to the compositions containing the above known components, whereby they are made in a form of a putty for the purpose of improvements in manipulatability and wear resistance.

According to the present invention, it has further been found that a non-functional group type liquid organic polymer having a solubility of 0.2 or less at 20° C. is added to the setting agent for the purpose of eliminating the stickiness of the materials and improving the adhesion, placing and forming of the materials with respect to the teeth during temporary sealing/filling, whereby the materials can be prevented from becoming sticky during manipulation and temporary sealing/filling and increase body resistance, so that they can be easily filled in place even with the hand and fingers.

In the non-eugenol materials of the present invention, it is unsuitable to use for the setting agent containing the reactive multi-valent metal salts a finely divided inorganic filler and non-functional group type liquid organic polymer, both having a solubility of 0.2 or more at 20° C., since it is likely that the temporarily sealed set product tends to dissolve and disintegrate.

Additionally, it is likely that the base agent containing acid components comprising a combination of the liquid acidic phosphates with the liquid organic carboxylic acids having six or more carbon atoms may give rise to internal reactions or be devitrified or clouded and precipitated and isolated upon contamination with carbonates, oxides and hydroxides of metals and silicates. Thus, the use of such components is unpreferable. Also unpreferable for the present invention is the use of diatomaceous earth, since the set product may become much coarse due to its particles being coarsened.

In the present invention, therefore, it is preferred that the finely divided silica is added to the base agent containing acid components comprising a combination of the liquid acidic phosphates with the liquid organic carboxylic acids having six or more carbon atoms and the finely divided inorganic filler having a solubility of 0.2 or less at 20° C. is added to the setting agent containing the reactive multi-valent metal salt, thereby putting the base and setting agents into a putty form. By further addition of the non-functional group type liquid organic polymer having a solubility of 0.2 or less at 20° C., the material can be improved in stickiness, bonding, placing and forming onto the teeth. The finely divided silica includes silicic anhydride (silicic acid having a crystalline water plus deposited water content 5% or less) and hydrous silicic acid (silicic acid having a crystalline water plus deposited water content of 5% or more), which may be added to the base or setting agent alone or in combination.

It is understood that for use, the finely divided powders of silicic acid may be previously alkylated and made hydrophobic on their surfaces with a silane coupling agent such as an alkyl group-containing chlorosilane or an alkyl group-containing methoxysilane.

The finely divided inorganic fillers having a solubility of 0.2 or less at 20° C. include silica, aluminium oxide, titanium oxide, calcium oxide, zirconium oxide, magnesium oxide, aluminium hydroxide, calcium hydroxide, magnesium hydroxide, aluminium silicate, calcium silicate, zirconium silicate, magnesium silicate, barium sulfate and so on, which may be added to the setting agent alone or in combination of two or more. The non-functional group type liquid organic polymers having a solubility of 0.2 or less at 20° C. include non-functional group types of chemically stable polybutene, liquid polybutadiene, liquid polyisobutylene, polypropylene glycol, liquid polyisoprene and so on, which may be added to the setting agent alone or in combinations of two or more with the finely divided inorganic filler.

In the filling compositions for dental temporary sealing purposes, the powders of the finely divided silica and the finely divided inorganic filler having a solubility of 0.2 or less at 20° C. should have a proper particle size so as to put the base and setting agents into a putty form and facilitate the taking, mixing and temporary sealing/filling of samples. That is, when the putty-form filling composition for dental temporary sealing is prepared with the finely divided silica and the finely divided inorganic filler having a solubility of 0.2 or less at 20° C., both having a mean particle size below 2 m$\mu$, the base and setting agents tend to stick to a spatula during taking or mixing, and the mixed product tends to stick to the hand or instruments, thus posing a handling problem. It is thus required to limit to 2 m$\mu$ the minimum mean particle size of the finely divided silica and the finely divided inorganic filler having a solubility of 0.2 or less at 20° C. When the putty-form temporary filling composition for dental temporary sealing is prepared with the finely divided silica and the finely divided inorganic filler having a solubility of 0.2 or less at 20° C., both having an average particle size exceeding 2,000 mμ, the mixture is so roughened on its surface that the surface of the temporarily sealed set product is roughened and tends to attract foreign matters. The maximum average particle size of the silica and the finely divided inorganic filler having a solubility of 0.2 or less at 20° C. is limited to 2,000 mμ.

In order to prepare the putty-form filling composition for dental temporary sealing which can be easily mixed together by the hand and fingers, the non-functional group type liquid organic polymer having a solubility of 0.2 or less at 20° C., which is added to the setting agent, should have a proper viscous property. That is, when the putty-form filling composition for dental temporary sealing is prepared with non-functional group types of chemically stable polybutene, liquid polybutadiene, liquid polyisobutylene, liquid polyisoprene and polypropylene glycol having a solubility of 0.2 or less at 20° C. and a molecular weight of 600 or less, difficulty is involved in its mixing and filling by the hand and figures, since the setting agent shows strong stickiness during its taking-out or mixing with the base agent or its viscosity and softness are poor. Consequently, the the lower-limit average molecular weight of scuh a non-functional group type liquid organic polymer is placed at 600. The non-functional group type liquid organic polymer having a solubility of 0.2 or less at 20° C. but an average molecular weight exceeding 60,000 is unpreferred, since the setting agent is solidified or powderized and so lacks in proper softness and manipulatability so that difficulty is involved in its mixing by the hand and fingers, and because the set product decreases sharply in strength and is embrittled. Consequently, the upper-limit average molecular weight of the non-functional group type liquid organic polyer having a solubility of 0.2 or less at 20° C. is placed at 60,000.

In the filling composition for dental temporary sealing, the amount of the finely divided silica should be a minimum of 5.0% by weight so as to make in a putty form the base agent for its facilitated taking-out with a spatula, and the ratio of the finely divided silica to be mixed is limited to a maximum of 50.0% by weight to maintain the function of the base agent without damaging its inherent physical properties.

In order to make in a putty form the setting agent and increase its viscosity for its facilitated taking-out with a spatula, the amount of the finely divided inorganic filler having a solubility of 0.2 or less at 20° C. is required to be a minimum of 1.0% by weight, and the upper-limit amount thereof should be 20.0% by weight so as to maintain the function of the setting agent without damaging its inherent physical properties. Furthermore, the non-functional group type liquid organic polymer having a solubility of 0.2 or less at 20° C. added for the purpose of eliminating the stickiness of the composition and improving the bonding, placing and forming of the composition onto the teeth during temporary sealing-/filling should be used in the minimum amount of 1.0% by weight but in the maximum amount of 10.0% by weight so as to maintain the function of the composition without damaging its inherent physical properties.

Consequently, it is preferred that:

(A) the ratio of the finely divided silica having an average particle size of 2 to 2,000 mμ, to be mixed with the base agent composition, be limited to a range of 5.0 to 50.0% by weight, and (B) the ratio of the finely divided inorganic filler having a solubility of 0.2 or less at 20° C. and a mean particle size of 2 to 2,000 mμ, to be mixed with the setting agent composition, be limited to a range of 1.0 to 20.0% by weight. If the non-functional group type liquid organic polymer having a solubility of 0.2 or less at 20° C. and an average molecular weight of 600 to 60,000 is further added, its ratio to be mixed with the setting agent composition should preferably be limited to a range of 0.5 to 10.0% by weight.

The known non-eugenol filling compositions used in the present invention, comprise the base composition containing a water-insoluble liquid acidic phosphate and/or a liquid organic carboxylic acid having six or more carbon atoms and the setting agent composition containing a reactive multi-valent metal salt. By mixing the base agent composition with the setting agent composition, forming a metal salt of a water-insoluble liquid acidic phosphate and/or a metal salt of a liquid organic carboxylic acid having six or more carbon atoms with exothermic reaction, and solidified. Optionally, known additive such as thermoplastic resins, setting accelerator of liquid organic carboxylic acids having five or less carbon atoms or di- or more-valent solid organic carboxylic acids having a melting point of 200° C. or lower, setting acceleration aid of slightly soluble fluorides, vegetable oils, coloring agents and perfumes may be added to the base and setting agent compositions. The following are typical for the known non-eugenol compositions.

| Non-eugenol Composition (of the paste/paste type) |
| --- |
| Base agent (paste) components |
| Liquid acidic phosphate |
| Liquid organic carboxylic acid |
| Thermoplastic resin |
| Setting agent (paste) components |
| Reactive multi-valent metal salt |
| Vegetable oil |

If required, use may be made of a setting accelerator such as a low-molecular organic carboxylic acid having five or less carbon atoms or a di- or more-valent solid carboxylic acid, a setting acceleration aid of slightly soluble fluorides, coloring matters, perfumes and so on.

An object of the present invention is to provide a non-eugenol composition in a form of a putty based on a paste-paste type of non-eugenol composition in which the finely divided silica is added to and mixed with the base agent composition containing the liquid acidic phosphate and/or the liquid organic carboxylic acid having a solubility of 0.2 or less at 20° C., and the finely divided inorganic filler having a solubility of 0.2 or less at 20° C. is added to and mixed with the setting agent composition containing the reactive multi-valent metal salt, whereby the material can be easily taken out, the base and setting agents A and B can be easily mixed together and mixed up by the hand and fingers for a limited mixing period of time, and the material has improved abrasion resistance and durability. Another object of the present invention is to provide a eugenol composition in a form of a putty which is improved in terms of stickiness during temporary sealing and filling and bonding, placing and forming onto the teeth by further adding and mixing of the non-functional group type liquid organic polymer having a solubility of 0.2 or less at 20° C.

EXAMPLES

The present invention will now be explained with reference to the following non-restrictive examples.

EXAMPLE 1

| Component A | |
| --- | --- |
| Dioctyl acid phosphate | 60% by weight |
| Finely divided silica (Hydrous silicic acid of 16 mμ in average particle size, available under the trade name of Nipsil VN-3 from Nihon Silica, Co., Ltd.) | 40% by weight |

The dioctyl acid phosphate and finely divided silica were kneaded up in a kneader for 40 minutes to obtain a putty product, which was then canned as the component A.

The component A was much easily taken out with the use of a spatula.

| Component B | |
| --- | --- |
| Zinc oxide | 80.0% by weight |
| Olive oil | 11.5% by weight |
| Titanium oxide (having an average particle size of 300 mμ) | 8.5% by weight |

The zinc oxide, olive oil and titanium oxide were kneaded up in a kneader for one hour to obtain a putty product, which was then canned as the component B.

The component B was much easily taken out with the use of a spatula.

The equal amounts of the components A and B could be mixed up on mixing pad by an exclusive spatula within a very short time of 25 seconds. They could be mixed up by the hand and fingers for again 25 seconds.

A setting time of 4.5 minutes gave a set product having suitable manipulatability. The abrasion loss (depth) was 70μ, an about 40% decrease compared with that of the comparison example (to be given later) and indicating an improvement in durability.

EXAMPLE 2

| Component A | |
| --- | --- |
| Diisodecyl acid phosphate | 35% by weight |
| Monobutyl acid phosphate | 27% by weight |
| Finely divided silica (silicic anhydride having an average particle size of 7 mμ available under the trade name of Aerosil 300 from Nihon Aerosil, Co., Ltd.) | 38% by weight |

The diisodecyl acid phosphate, monobutyl acid phosphate and finely divided silica (Aerosil 300) were kneaded up in a kneader for 30 minutes to obtain a putty product, which was then canned as the component A.

The component A was much easily taken out with the use of a spatula.

| Component B | |
| --- | --- |
| Basic aluminium acetate | 58% by weight |
| Camelia oil | 15% by weight |
| Liquid polyisobutylene (having an average molecular weight of 30,000 and insoluble in water) | 10% by weight |
| Magnesium oxide | 17% by weight |

The basic aluminium acetate, magnesium oxide, camelia oil and liquid polyisobutylene were kneaded up in a kneader for one hour to obtain a putty product, which was then canned as the component B.

The component B was much easily taken out with the use of a spatula.

The equal amounts of the components A and B could be mixed up on mixing pad by an exclusive spatula within a very short time of 20 seconds. They could be mixed up by the hand and fingers for again 20 seconds.

A setting time of 4.5 minutes gave a set product having such suitable manipulatability as not sticking to the hand and fingers, an instrument and so on. The abrasion loss (depth) was 80μ, an about 35% decrease compared with that of the comparison example and indicating an improvement in durability.

EXAMPLE 3

| Component A | |
| --- | --- |
| n-capric acid | 13% by weight |
| Hydrogenated rosin | 20% by weight |
| Mono-octyl acid phosphate | 25% by weight |
| Dibutyl acid phosphate | 10% by weight |
| Finely divided silica (hydrous silicic acid having an average particle size of 30 mμ available under the trade name of Tokuseal GU from Tokuyama Soda, Co., Ltd.) | 30% by weight |
| Levulinic acid | 2% by weight |

The n-capric acid and hydrogenated rosin were charged in a kneader in which they are heated and dissolved under well agitation at 100° C. for 20 minutes. Then, the mono-octyl acid phosphate, dibutyl acid phosphate and finely divided silica (Tokuseal GU) were added for 20-minute kneading, and the product was cast into a can wherein it was allowed to cool down to obtain the putty component A.

The component A was much easily taken out with the use of a spatula.

| Component B | |
| --- | --- |
| Zinc oxide | 68% by weight |
| Camellia oil | 13% by weight |
| Barium sulfate (having a mean particle size of 1,800 mμ) | 12% by weight |
| Zirconium silicate (having a mean particle size of 400 mμ) | 7% by weight |

The zinc oxide, camellia oil, barium sulfate and zirconium silicate were kneaded up in a kneader for 30 minutes to obtain a putty product, which was then canned as the component B.

The component B was much easily taken out with the use of a spatula.

The equal amounts of the components A and B could be mixed up on mixing pad by an exclusive spatula within a very short time of 20 seconds.

A setting time of 3 minutes gave a set product having suitable manipulatability. The abrasion loss (depth) was 70μ, an about 40% decrease compared with that of the comparison example and indicating an improvement in durability.

EXAMPLE 4

| Component A | |
| --- | --- |
| Dioctyl acid phosphate | 10% by weight |

-continued

| Component A | |
|---|---|
| Undecylenic acid | 35% by weight |
| Ester gum | 45% by weight |
| Finely divided silica (hydrous silicic acid having a mean particle size of 30 mμ available under the trade name of Silton R-2 from Mizusawa Kagaku, Co., Ltd.) | 8% by weight |
| Levulinic acid | 2% by weight |

The undecylenic acid and ester gum were charged in a kneader wherein they were heated and dissolved under well agitation at 100° C. for 30 minutes. Then, the dioctyl acid phosphate, finely divided silica and levulinic acid were added for 20-minute kneading, and the product was cast in a can wherein it was allowed to cool down to obtain the putty component A.

The component A was much easily taken out by using a spatula.

| Component B | |
|---|---|
| Magnesium silicate | 19% by weight |
| Zinc hydroxide | 62% by weight |
| Peanut oil | 14% by weight |
| Polybutene (having a mean molecular weight of 650) | 5% by weight |

The magnesium sulfate, zinc hydroxide, peanut oil and polybutene were kneaded up in a kneader for 30 minutes to obtain a putty product, which was then canned as the component B.

The component B was much easily taken out with the use of a spatula.

The equal amounts of the components A and B could be mixed up on mixing pad by an exclusive spatula within a very short time of 15 seconds. They could be mixed up by the hand and fingers for again 15 seconds.

A setting time of 3.5 minutes gave a set product having such suitable manipulatability as not sticking to the hand and fingers, an instrument and so on. The abrasion loss (depth) was 90μ, an about 25% decrease compared with that of the comparison example and indicating an improvement in durability.

EXAMPLE 5

| Component A | |
|---|---|
| Dimer acid | 34% by weight |
| Capric acid | 10% by weight |
| Rosin | 5% by weight |
| Finely divided silica (silicic anhydride having an average particle size of 40 mμ available under the trade name of Aerosil OX-50 from Nihon Aerosil Co., Ltd.) | 48% by weight |
| Acetic Acid | 3% by weight |

The dimer acid, capric acid and rosin were charged in a kneader in which they are heated and dissolved under well agitation at 105° C. for 40 minutes. Then, the finely divided silica and acetic acid (Aerosil OX-50) were added for 20-minute kneading, and the product was cast into a can wherein it was allowed to cool down to obtain the putty component A.

The component A was much easily taken out with the use of a spatula.

| Component B | |
|---|---|
| Zinc oxide | 68% by weight |
| Zinc acetate | 5% by weight |
| Camellia oil | 12% by weight |
| Aluminium silicate (having a mean particle size of 200 mμ) | 15% by weight |

The zinc oxide, zinc acetate, camellia oil and aluminium silicate were kneaded up in a kneader for 50 minutes to obtain a putty product, which was then canned as the component B.

The component B was much easily taken out with the use of a spatula.

The equal amounts of the components A and B could be mixed up on mixing pad by an exclusive spatula within a very short time of 20 seconds. A setting time of 4 minutes gave a set product having suitable manipulatability. The abrasion loss (depth) was 75μ, about 40% decrease compared with that of the comparison example and indicating an improvement in durability.

EXAMPLE 6

| Component A | |
|---|---|
| Pelargonic acid | 15% by weight |
| Trimer acid | 30% by weight |
| Glutaric acid | 2% by weight |
| Rosin | 25% by weight |
| Levulinic acid | 3% by weight |
| Finely divided silica (hydrous silicic acid having a mean particle size of 8 mμ available under the trade name of Nipsil NS from Nihon Silica, Co., Ltd.) | 25% by weight |

The pelargonic acid, trimer acid, glutaric acid and rosin were charged in a kneader wherein they were heated and dissolved under well agitation at 100° C. for 30 minutes. Then, the levulinic acid and finely divided silica (Nipsil NS) were added for 30-minute kneading, and the product was cast in a can wherein it was allowed to cool down to obtain the putty component A.

The component A was much easily taken out by using a spatula.

| Component B | |
|---|---|
| Zinc oxide | 70% by weight |
| Olive oil | 12% by weight |
| Aluminium oxide | 10% by weight |
| Liquid polyisoprene (having a mean molecular weight of 29,000) | 5% by weight |
| Liquid polybutadiene (having a mean molecular weight of 4,000) | 3% by weight |

The zinc oxide, olive oil, aluminium hydroxide, liquid polyisoprene and liquid polybutadiene were kneaded up in a kneader for 50 minutes to obtain a putty product, which was then canned as the component B.

The component B was much easily taken out with the use of a spatula.

The equal amounts of the components A and B could be mixed up on mixing pad by an exclusive spatula within a very short time of 15 seconds. They could be mixed up by the hand and fingers for again 15 seconds.

A setting time of 3 minutes gave a set product having such suitable manipulatability as not sticking to the hand and fingers, an instrument and so on. The abrasion loss (depth) was 85μ, about 30% decrease compared with that of the comparison example and indicating an improvement in durability.

COMPARISON EXAMPLE

| Component A (Paste) | |
| --- | --- |
| Dimer acid | 56% by weight |
| Capric acid | 10% by weight |
| Rosin | 28% by weight |
| Glutaric acid | 2% by weight |
| Acetic acid | 4% by weight |

The dimer acid, capric acid, rosin and glutaric acid were charged in a kneader wherein they were heated and dissolved under well agiation at 110° C. for 40 minutes. Then, the acetic acid was added for 20-minute kneading, and the kneaded product was filled in a tube and allowed to cool down to obtain a pasty component A.

| Component B (Paste) | |
| --- | --- |
| Zinc oxide | 88% by weight |
| Olive oil | 7% by weight |
| Castor oil | 5% by weight |

The zinc oxide, olive oil and castor oil were charged in a kneader for one-hour kneading giving a paste, which was then tubed as the component B.

The equal amounts of the components A and B were forced out of the tube onto mixing pad on which they could be mixed up for a mixing time of 30 seconds. A setting time of 4 minutes 40 seconds gave a set product. The abrasion loss (depth) was 120µ indicating that the material was soft and worn considerably.

TABLE 1

| Items | Example 1 | Example 2 | Example 3 | Example 4 | Example 5 | Example 6 | Comparative Example |
| --- | --- | --- | --- | --- | --- | --- | --- |
| Easiness in taking out | ⊙ | ⊙ | ⊙ | ⊙ | ⊙ | ⊙ | ○ |
| Mixing time (sec.) | 25 | 20 | 20 | 15 | 20 | 15 | 30 |
| Setting time (min.: sec). | 4:30 | 4:30 | 3:00 | 3:30 | 4:00 | 3:00 | 4:40 |
| Abrasion loss (depth: µ) | 70 | 80 | 70 | 90 | 75 | 85 | 120 |
| Leakage | ⊙ | ⊙ | ⊙ | ⊙ | ⊙ | ⊙ | × |

Easiness of Taking-Out Suitable Amount
⊙: Very Easy, ○: Easy
Abrasion Losses - Abrasion Tester
A sample (of 10.0 mm in diameter and 5.0 mm in a height) was subjected to 10000 cycles of 50-mm reciprocation of a nylon-made toothbrush (having a diameter of 0.25 mm and 790 bristles/cm² under a load of 48 g/cm² to measure an abrasion loss in terms of an average abrasion depth (µ).
Leakage of Material From Container at 60° C. for 30 days
⊙: No leakage occurred at all.
×: Noticeable leakage occurred.

As will be appreciated from a comparative of the Examples with the Comparative Example, i.e., from Table 1, the present non-eugenol base filling compositions for dental temporary sealing, in which the components A and B are made in a form of a putty by the respective addition of the finely divided silica and the finely divided inorganic filler having a solubility of 0.2 or less at 20° C., allow the material to be easily taken out in a suitable amount and mixed up within a time period about ⅔ to ½ shorter than that required for the conventional product on account of rapider mixing and dispersion. By further addition of the non-functional group type organic polymer to the component B, the material can be mixed up even with the hand and fingers for a shorter period time, and its stickiness during temporary sealing/filling can be eliminated with improvements in its bonding, placing and forming onto the teeth.

No leakage of the material out of the container during storage occurs at all, and there is no substantial change in the setting time of the material by storage, thus resulting in stable maintenance of its quality. In addition, the abrasion losses of the set products show a 25 to 40% decrease, indicating improved wear resistance. Thus, the material according to the present invention can be handled irrespective of skillfulness and provide a stable temporary sealant with improved wear resistance but with no fear of deformation and dislocation.

With the materials according to the present invention, it is possible to reduce the chair time in dental treatments and maintain clearer clinic environments, thus enabling dentists, dental hygienists, assistants and the like to carry out efficient and sound clinic activities and also enabling patients to receive comfortable and efficient treatments.

What is claimed is

1. A filling composition for temporary dental sealing comprising:

a component A of putty consistency which contains, as a base agent, a water-insoluble liquid acidic phosphate selected from the group consisting of monoalkyl acid phosphates, monoaryl acid phosphates, dialkyl acid phosphates, diaryl acid phosphates and alkyl aryl acid phosphates and/or a water-insoluble organic carboxylic acid having at least six carbon atoms that is liquid at room temperature and contains 5.0 to 50.0% by weight of finely divided silica having an average particle size of 2 to 2,000 µm and a component B of putty consistency which contains, as a setting agent, a multivalent metal salt and contains 1.0 to 20.0% by weight of at least one finely divided inorganic filler having an average particle size of 2 to 2,000 µm selected from the group consisting of silica, aluminum oxide, titanium oxide, calcium oxide, zirconium oxide, magnesium oxide, aluminum hydroxide, calcium hydroxide, magnesium hydroxide, aluminum silicate, calcium silicate, zirconium silicate, magnesium silicate and barium sulfate.

2. A composition as claimed in claim 1, wherein said component B further contains 1.0 to 10.0% by weight of a non-functional group type liquid organic polymer selected from the group consisting of polybutene, liquid polybutadiene, liquid polyisoprene, liquid polyisobutylene, polypropylene glycol and mixtures thereof.

3. The composition of claim 2, wherein the organic polymer has a mean molecular weight of 600 to 60,000.

* * * * *